(12) United States Patent
Yamamoto (10) Patent No.: US 9,405,114 B2
(45) Date of Patent: Aug. 2, 2016

(54) CAMERA MODULE FOR ENDOSCOPE

(75) Inventor: Goki Yamamoto, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 1158 days.

(21) Appl. No.: 13/437,791

(22) Filed: Apr. 2, 2012

(65) Prior Publication Data

US 2012/0257028 A1  Oct. 11, 2012

(30) Foreign Application Priority Data

Apr. 8, 2011 (JP) ................................. 2011-086100
Apr. 8, 2011 (JP) ................................. 2011-086101

(51) Int. Cl.
    *G02B 23/24* (2006.01)
    *G03B 3/10* (2006.01)
    *A61B 1/00* (2006.01)

(52) U.S. Cl.
    CPC .......... *G02B 23/243* (2013.01); *A61B 1/00183* (2013.01); *G03B 3/10* (2013.01); *G03B 2205/0046* (2013.01)

(58) Field of Classification Search
    CPC ................ G02B 23/243; G03B 3/10; G03B 2205/0046; A61B 1/00183
    See application file for complete search history.

(56) References Cited

U.S. PATENT DOCUMENTS

| 6,371,909 B1 * | 4/2002 | Hoeg ................. A61B 1/00096 600/112 |
| 2002/0016526 A1 * | 2/2002 | Akiba ........................... 600/167 |
| 2006/0133786 A1 * | 6/2006 | Teramoto ........................ 396/55 |

FOREIGN PATENT DOCUMENTS

JP     2000-121957 A    4/2000

OTHER PUBLICATIONS

Chinese Office Action dated Mar. 3, 2015 with an English Translation thereof.

* cited by examiner

*Primary Examiner* — Tat Chio
(74) *Attorney, Agent, or Firm* — McGinn IP Law Group, PLLC (57) ABSTRACT

A camera module consists of an image sensor, an objective lens system, and a lens drive mechanism. The objective lens system includes a taking lens and a prism having a reflection surface inclined at an angle of 45° to an optical axis of the taking lens, to reflect incident light toward the image sensor on a circuit board, which is positioned in parallel to the optical axis of the taking lens. The lens drive mechanism includes a motor and a rotary shaft driven by the motor. The motor is positioned behind the prism, and a drive shaft of the motor is coupled to the rotary shaft through a power transmission mechanism. The rotary shaft is positioned on one radial side of the taking lens and is coupled to a movable lens element of the taking lens such that the movable lens element is moved in the axial direction by rotary motion of the rotary shaft.

7 Claims, 8 Drawing Sheets

CAMERA MODULE FOR ENDOSCOPE

BACKGROUND OF THE INVENTION

1. Field of the Invention

The present invention relates to a camera module for an endoscope, which is mounted in a distal end of a probing portion of the endoscope inserted into a lumen or cavity of a test body.

2. Description of the Related Art

An endoscope has a camera module mounted in a distal end of a probing portion thereof, which is inserted into a lumen or cavity of a test body to be inspected with the endoscope. The camera module is a unit into which a taking lens and a circuit board, including an image sensor and a drive circuit for driving the image sensor, are integrated. The taking lens may include a movable lens and a lens drive mechanism for the movable lens to change the image magnification. The camera module is connected to a monitor that is installed outside the test body, so that images acquired from inside the lumen by the camera module may be displayed on the monitor.

The camera module is desired to be as small as possible for reducing the load on a patient when the endoscope is inserted into the patient. One problem against minimization of the camera module is that the circuit board takes a certain width or diameter in the camera module when the circuit board is positioned perpendicular to the optical axis of the taking lens. To solve this problem, JPA 2000-121957 suggests a camera module, in which a circuit board is positioned substantially parallel to the optical axis of a taking lens, and a prism disposed behind the taking lens refracts light from the subject toward the image sensor on the circuit board.

In the camera module of the above prior art, a movable lens for changing the image magnification is moved by rotating a rotary shaft which is directly coupled to a drive shaft of a motor. In this prior art, the motor for moving the movable lens is held in a notch that is formed in a cylindrical surface of a first ring of an angle ring and deformed to hold the motor in the distal end of the endoscope probing portion.

While the image sensor may not widen the endoscope probing portion in the above prior art, there will be dead or useless space behind the prism because the rotary shaft is directly coupled to the drive shaft of the motor. The dead space is obstructive to the reduction of diameter of the probing portion. Moreover, the direct coupling of the motor drive shaft to the rotary shaft results in increasing the length of the camera module along the optical axis of the taking lens, i.e. in the longitudinal direction of the probing portion.

SUMMARY OF THE INVENTION

In view of the foregoing, an object of the present invention is to provide a minimized camera module for an endoscope.

According to the present invention, a camera module for an endoscope disposes a motor of a lens drive mechanism behind a prism that is positioned behind a taking lens. The motor may be positioned with its drive shaft oriented parallel to an optical axis of the taking lens. Alternatively, the motor may be positioned with its drive shaft inclined to the optical axis.

The taking lens has a lens element movable along the optical axis, and the prism reflects incident light at an approximately right angle to the optical axis. Through the taking lens and the prism, an optical image is formed on an imaging surface of an imaging device that is mounted on a circuit board. The imaging device converts the optical image to an electric signal. The motor is driven to rotate a drive shaft upon an externally supplied electric power. A rotary shaft is positioned on one radial side of the taking lens. The rotary shaft is rotatable on an axis extending along the optical axis. The rotary shaft is coupled to the movable lens element such that bidirectional rotary motions of the rotary shaft cause the movable lens element to move back and forth along the optical axis. The rotary motions of the drive shaft are transmitted to the rotary shaft through a power transmission mechanism.

Preferably, the rotary shaft may consist of a number of rotators aligned to be rotatable on a common axis that is parallel to the optical axis, wherein adjacent two of the rotators are coupled to each other with a predetermined rotary play, to transmit the rotary motion of the drive shaft sequentially from a rear side one of the rotators, which is coupled to the power transmission mechanism, toward a front side one of the rotators, which is coupled to the movable lens.

The rotary shaft may preferably consist of at least three rotators, and the rotary play between the adjacent two rotators is preferably set at a larger angle in the front side than in the rear side.

Preferably, the rotators include at least a rod rotator and at least a ring rotator, which are aligned alternately on the common axis. The rod rotator has outward protrusions provided at regular angular intervals around an outer periphery thereof. The ring rotator has inward protrusions provided at regular angular intervals around an inner periphery thereof, and has a greater internal diameter exclusive of the inward protrusions than an external diameter of the rod rotator inclusive of the outward protrusions. The ring rotator is rotatably fitted on the rod rotator and caused to rotate together with the rod rotator as the outward protrusions push the inward protrusions when the rod rotator rotates inside the ring rotator.

It is preferable to reset the respective rotators to neutral positions after the movable lens element is moved into a designated position. From these neutral positions the drive shaft may be rotated by an approximately equal amount in either direction till all the rotators begin to rotate together. In order to reset the rotators to the neutral positions after the movable lens element is moved into a designated position, the motor may be driven to rotate the drive shaft in a reverse direction opposite to a preceding rotational direction or alternately in the reverse and opposite directions to the extent that it does not cause the movement of the movable lens element. Thereafter the motor may be stopped.

The lens drive mechanism may include a tubular member that is coupled to the movable lens element. The tubular member is coupled to the rotary shaft through an engaging mechanism that converts the rotary motion of the rotary shaft to a linear motion of the tubular member along the rotary shaft. Thus, the movable lens element is caused to move along the optical axis with the rotation of the rotary shaft.

The motor and the power transmission mechanism may preferably be held in a motor case that shields the drive shaft and the power transmission mechanism from outside, and the rotary shaft may preferably be held in a shaft case that shield the rotary shaft from outside. The motor case may be affixed to a rear end of the shaft case to form an integral unit. The motor may preferably be adhered to the motor case using an adhesive material with a high heat-conductivity.

According to the present invention, the motor for driving the movable lens element is disposed behind the prism, making good use of the space behind the prism. Thus, the space efficiency of the camera module is so improved as to make the camera module compact and small.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
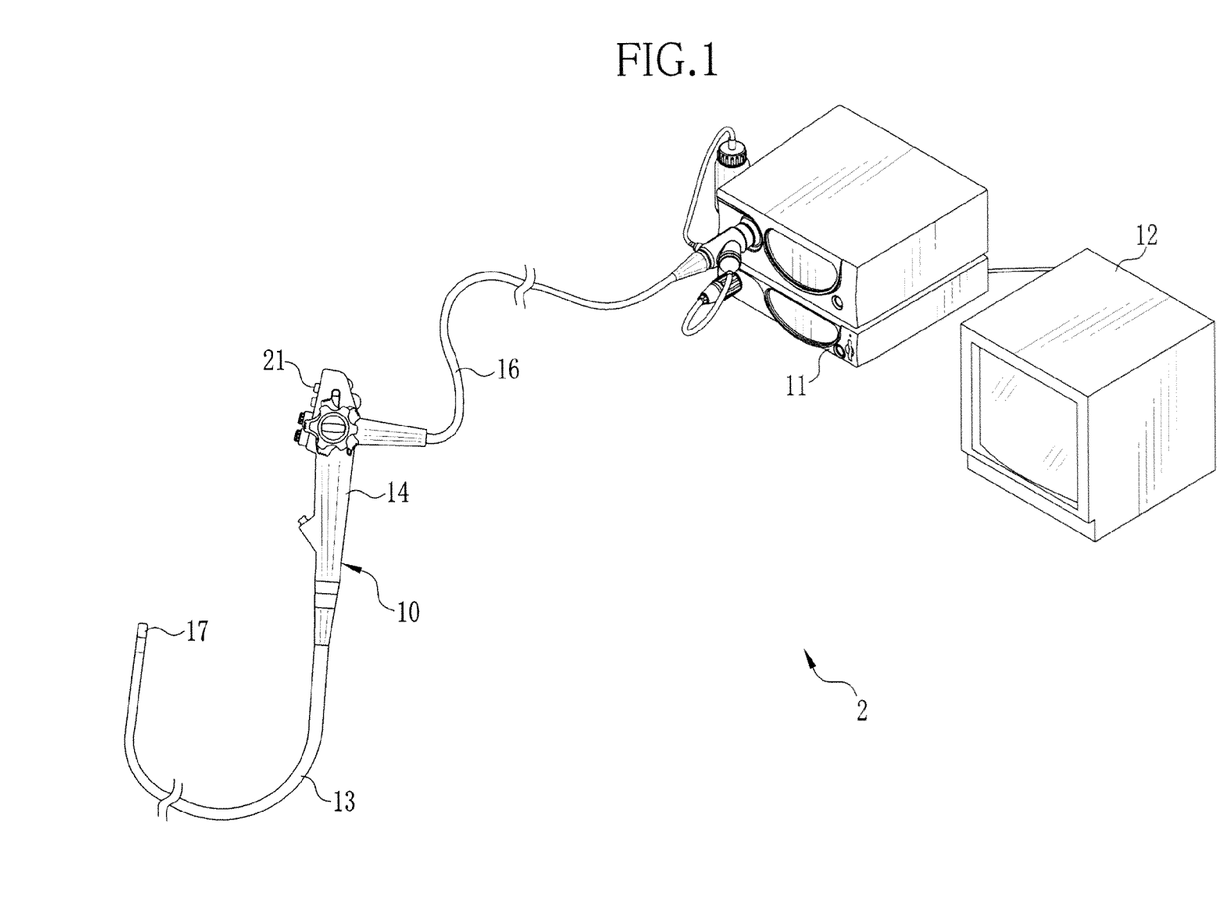
FIG. 1 is a perspective view illustrating an appearance of an electronic endoscope system.

As shown in FIG. 1, an electronic endoscope system 2 consists of an electronic endoscope 10, a processor unit 11, and a monitor 12. The electronic endoscope 10 has a flexible probing portion 13 insertable into a lumen of a test subject, a handling portion 14 coupled to a proximal end of the probing portion 13, and a universal cord 16 connected to the processor unit 11.

The handling portion 14 is provided with operational members, including an angle knob for bending the probing portion 13 so as to turn a distal end 17 of the probing portion 13 in any direction at any angle, an airing/watering button for actuating an airing/watering nozzle 20 to eject air or water, a zoom button 21 for changing the magnification of images captured by the endoscope 10, and a release button for recording an endoscopic image frame as a still image. A tool inlet for inserting a tool for medical procedures or the like is formed in a distal end portion of the handling portion 14. The tool inlet leads to a tool outlet 22 (see FIG. 2) of the distal end 17 through a tool channel that is provided along through the probing portion 13.

Figure 3A:
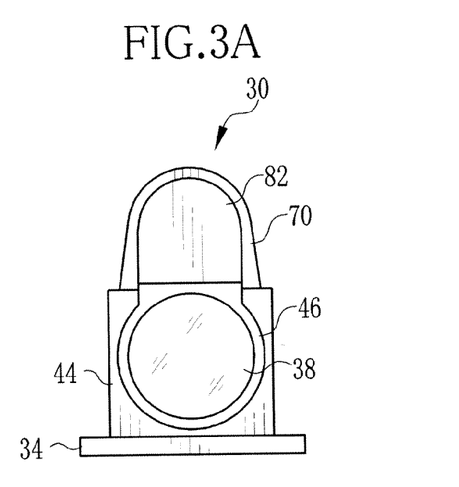
FIG. 3A is a front view of a camera module.
Figure 3B:
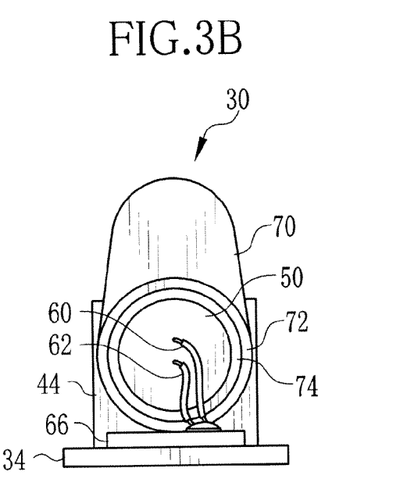
FIG. 3B is a rear view of the camera module.

The processor unit 11 supplies power to a camera module 30 (see FIGS. 3 to 4) and controls driving of the camera module 30 through the universal cord 16 and a transmission cable 68 (see FIG. 4) that extends through inside the probing portion 13. The processor unit 11 also receives an image signal output from the camera module 30 through the transmission cable 68, and processes the received image signal to produce image data. Based on the image data, endoscopic images are displayed on the monitor 12 that is connected through a cable to the processor unit 11.

Figure 2:
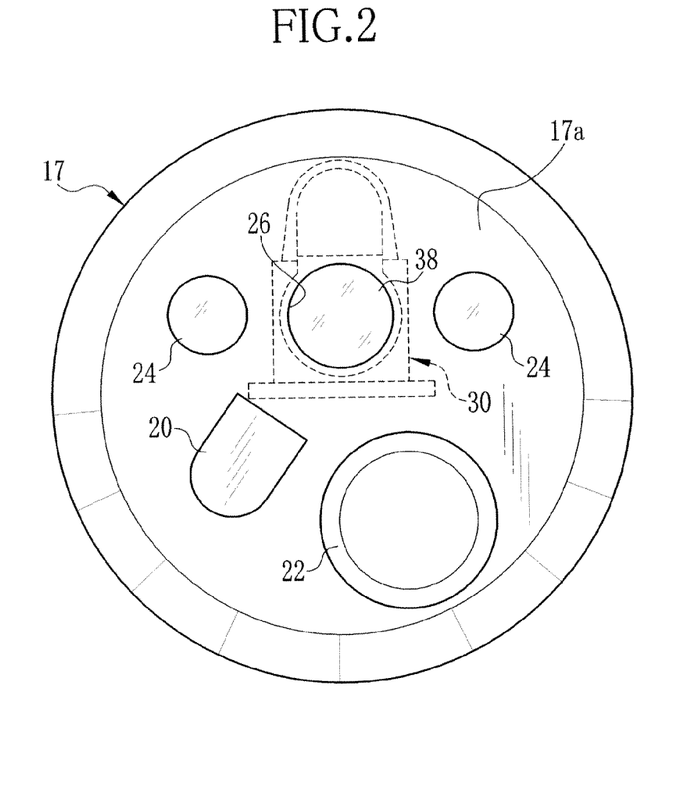
FIG. 2 is a plan view illustrating an end face of a distal end of a probing portion of an electronic endoscope.

As shown in FIG. 2, an end face 17a of the distal end 17 is provided with lighting windows 24 and an observing window 26 in addition to the airing/watering nozzle 20 and the tool outlet 22. The observing window 26 is provided as an opening formed through the end face 17a, and the camera module 30 is placed behind the observing window 26 such that a first lens element 38 of an objective lens system 32 of the camera module 30 (see FIG. 4) is fit in the observing window 26.

Figure 4:
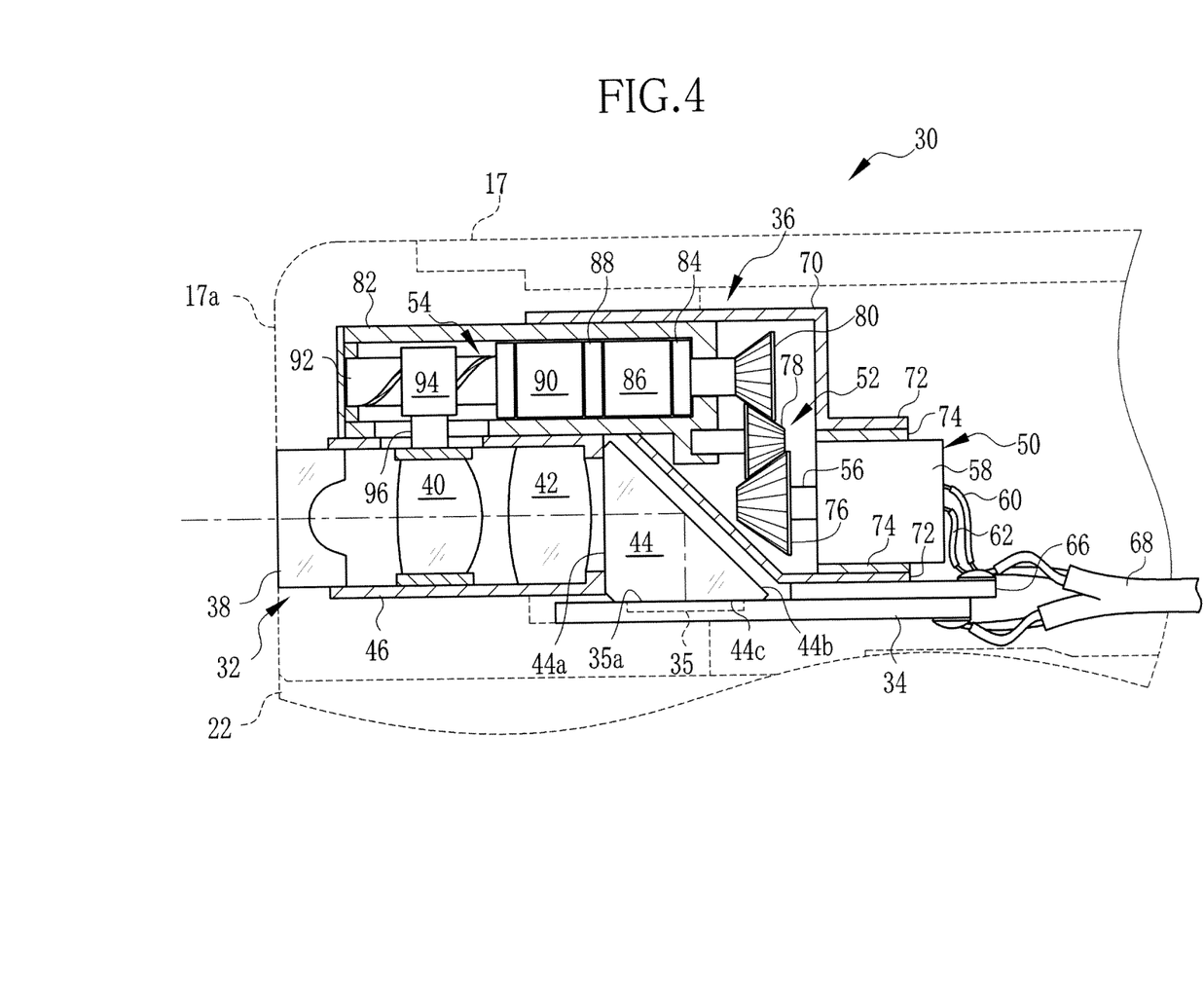
FIG. 4 is a sectional view of the camera module, taken along an optical axis of a taking lens.

As shown in FIGS. 3 and 4, the camera module 30 includes the objective lens system 32, a circuit board 34 and a lens drive mechanism 36. The objective lens system 32 consists of a taking lens and a prism 44. The taking lens is composed of three lens elements 38, 40 and 42, which are aligned on an optical axis that extends in a longitudinal direction of the probing portion 13.

The first and third lens elements 38 and 42 are mounted stationary; the first lens element 38 is fitted on its front side into the observing window 26 and on its rear side into a front end of a cylindrical lens barrel 46, whereas the third lens element 42 is fixedly fitted in a rear end of the lens barrel 46. On the other hand, the second lens element 40 is a movable lens or zoom lens that is moved by the lens drive mechanism 36 to change the image magnification of the taking lens. The second lens element 40 is held movable in the lens barrel 46 along the optical axis.

The prism 44 includes an incident surface 44a, a reflection surface 44b and an emission surface 44c. Margins of the incident surface 44a are fixedly adhered to the rear end of the lens barrel 46. Light from the subject, which enters through the taking lens, is incident on the incident surface 44a, which is substantially perpendicular to the optical axis of the first to third lens elements 38, 39 and 42 of the taking lens. The reflection surface 44b is inclined at an angle of 45° to the incident surface 44a so that the reflection surface 44b refracts the light path of the incident light by 90°. The emission surface 44c forms an angle of 90 degrees to the incident surface 44a, to emit the light reflected from the reflection surface 44b to an imaging surface 35a of a CCD image sensor 35.

The image sensor 35 is fabricated on the circuit board 34, and an array of photoelectric converters (sensor pixels) is formed in the imaging surface 35a of the image sensor 35. The image sensor 35 photoelectrically converts the light incident from the emission surface 44c onto the imaging surface 35a, to produce the image signal. The circuit board 34 is also provided with an electric circuit including a drive circuit for the image sensor 35, and is electrically connected to the processor unit 11 through the transmission cable 68. The circuit board 34 is fixedly adhered to the emission surface 44c of the prism 44 with the imaging surface 35a opposed to the emission surface 44c. Because the circuit board 34 is positioned substantially parallel to the optical axis of the taking lens, which extends along the length of the probing portion 13, the distal end 17 may have a smaller diameter than when the circuit board 34 was positioned perpendicularly to the optical axis.

The lens drive mechanism 36 includes a motor 50, a power transmission mechanism 52, and a rotary shaft 54. The motor 50 may for example be a DC motor. The motor 50 consists of a body 58 having a drive shaft 56, and drive cables connected to a rear side of the body 58. According to the current flowing direction through the drive cables 60 and 62, the motor 50 rotates the drive shaft 56 clockwise or counterclockwise. The drive cables 60 and 62 are connected to the transmission cable 68 via a subsidiary circuit board 66 that is mounted on the same side of the circuit board 34 as the image sensor 35.

The motor 50 is held in a motor case 70 and is placed behind the prism 44 such that the drive shaft 56 extends parallel to the optical axis of the taking lens, which extends along the length of the probing portion 13. The motor case 70 is provided with a tubular holder 72 in a rear end thereof. The holder 72 is formed from a highly exoergic material like aluminum, and the body 58 of the motor 50 is fitted in the holder 72 and is affixed to an inner periphery of the holder 72 using an adhesive material 74 with a high thermal conductivity.

Placing the motor 50 behind the prism 44 makes full use of the space behind the prism, allowing minimizing the camera module 30. Moreover, this configuration allows mounting a motor of larger diameter, i.e. greater rotary torque, in the camera module 30 without enlarging the whole size thereof in comparison with a case where a drive shaft of a motor is directly coupled to a driven rotary shaft of a lens drive mechanism. In addition, mounting the motor 50 in the highly exoergic holder 72 with the highly thermal-conductive adhesive 74 achieves efficient heat rejection from the motor 50 and thus prevents heating of the motor 50.

The power transmission mechanism 52 is constituted of first to third gears 76, 78 and 80. These gears 76 to 80 are mounted to be rotatable about individual axes in the motor case 70, and the axes of these gears 76 to 80 are parallel to the drive shaft 56. The first gear 76 is affixed to a distal end of the drive shaft 56 so that it rotates together with the drive shaft 56. The second gear 78 is in mesh with the first gear 76 so that it rotates along with the first gear 76. The second gear 78 is also in mesh with the third gear 80 so that the third gear 80 rotates along with the second gear 78. The motor case 70 shields the mechanism 52 from outside so as to prevent diffusion of dust and dirt to the outside, which may result from the gearing motion.

The third gear 80 is coupled to the rotary shaft 54. The rotary shaft 54 is mounted to be rotatable in a cylindrical case 82, which shields the rotary shaft 54 so as to prevent diffusion of dust and dirt, which may result from the rotation of the rotary shaft 54, to the outside of the case 82. The shaft case 82 is disposed on one radial side of the objective lens system 32 such that a rotary axis of the rotary shaft 54 extends substantially parallel to the optical axis of the taking lens 38 to 42, which extends along the length of the probing portion 13.

Figure 5:
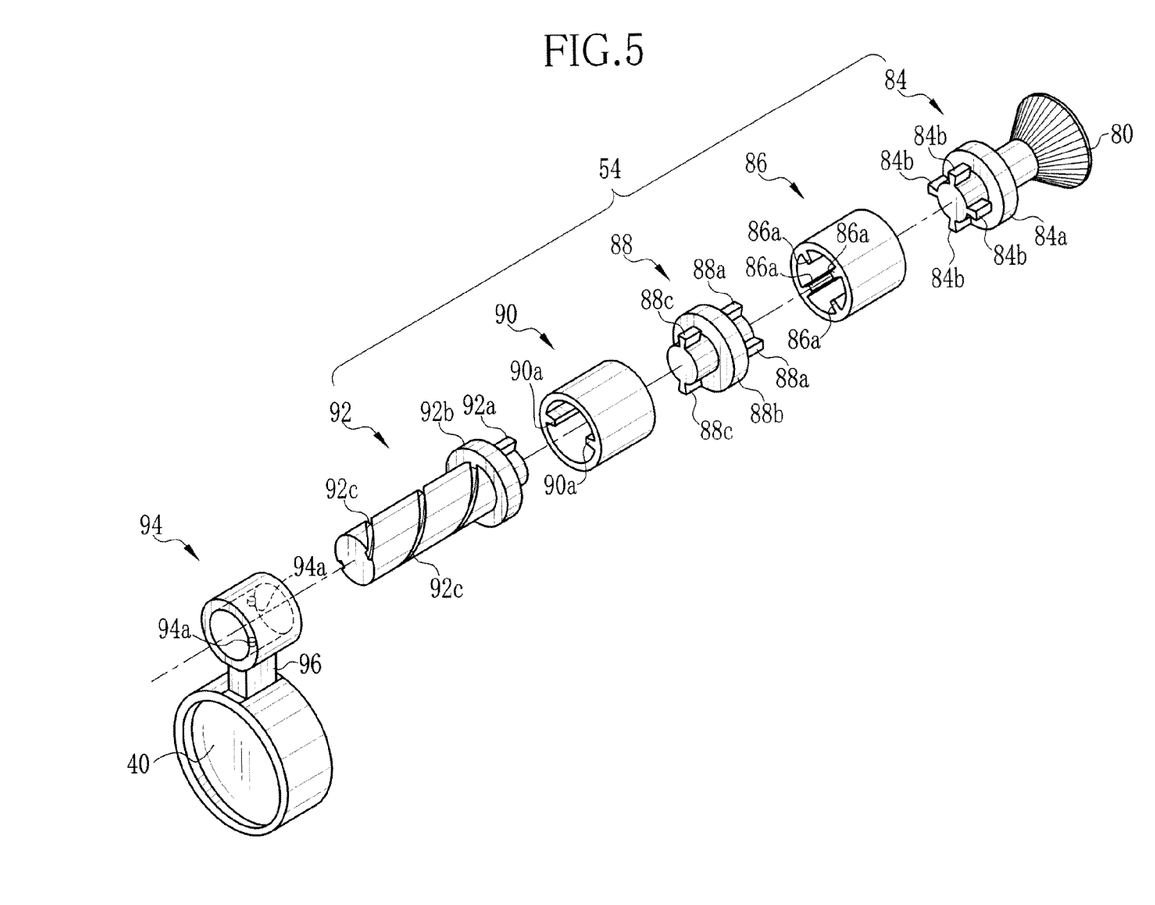
FIG. 5 is an exploded perspective view of a rotary shaft of a lens drive mechanism.

As shown in FIG. 5, the rotary shaft 54 consists of a first rod rotator 84, a first ring rotator 86, a second rod rotator 88, a second ring rotator 90, and a third rod rotator 92, which are aligned in this order from the third gear 80 toward the end face 17*a*, so as to be rotatable on the common rotary axis of the rotary shaft 54.

Figure 6A:
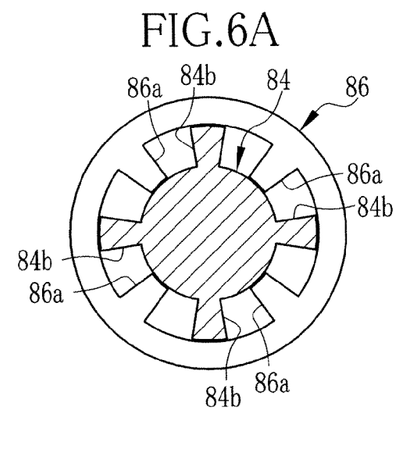
FIGS. 6A and 6B are explanatory views illustrating how rotation of a first rotary rod is transmitted to a first rotary cylinder.

The first rod rotator 84 is affixed at its rear end to the third gear 80 so that it rotates together with the third gear 80. The first rod rotator 84 is formed with a stop flange 84*a* and four ridges 84*b*. The stop flange 84*a* is provided in a middle portion of the length of the first rod rotator 84. The movement of the first rod rotator 84 is limited in the axial direction as the stop flange 84*a* is sandwiched between a rear wall of the shaft case 82 and the first ring rotator 86 (see FIG. 4). The ridges 84*b* are provided on a front end portion of the first rod rotator 84 at angular intervals of 90° (see FIG. 6) around the outer periphery.

The first ring rotator 86 has a greater diameter than the front end portion of the first rod rotator 84 such that the front end portion of the first rod rotator 84 may be inserted from the rear side into the first ring rotator 86. The first ring rotator 86 has four ridges 86*a* formed on its inner periphery at angular intervals of 90°. As the front end portion of the first rod rotator 84 is inserted in the first ring rotator 86, the ridges 86*a* are put in the rotational track of the ridges 84*b* of the first rod rotator 84 (see FIG. 6).

The second rod rotator 88 has a rear end portion having four ridges 88*a* formed at angular intervals of 90° around its outer periphery. The rear end portion of the second rod rotator 88 is inserted from the front side into the first ring rotator 86 so that the ridges 88*a* are put in the rotational track of the ridges 86*a* of the first ring rotator 86, like the relation between the ridges 84*a* and the ridges 86*a*. The second rod rotator 88 also has a stop flange 88*b* in a middle portion of the length of the second rod rotator 88; the stop flange 88*b* limits axial movement of the second rod rotator 88 within the rotary shaft 54. The second rod rotator 88 further has a front end portion having two ridges 88*c* formed at angular intervals of 180° around its outer periphery.

Figure 7A:
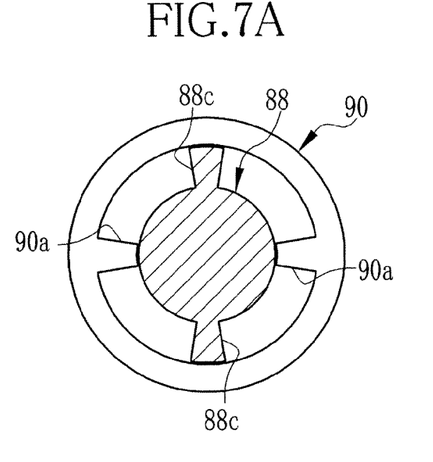
FIGS. 7A and 7B are explanatory views illustrating how rotation of a second rotary rod is transmitted to a second rotary cylinder.

The front end portion of the second rod rotator 88 is inserted from the rear side into the second ring rotator 90. The second ring rotator 90 has two ridges 90*a* formed on its inner periphery at angular intervals of 180°. As the front end portion of the second rod rotator 88 is engaged in the second ring rotator 90, the ridges 90*a* are put in the rotational track of the ridges 88*c* of the second rod rotator 88 (see FIG. 7).

The third rod rotator 92 has a rear end portion having two ridges 92*a* formed at angular intervals of 180° around its outer periphery. The rear end portion of the third rod rotator 92 is inserted from the front into the second ring rotator 90, so that the ridges 92*a* are put in the rotational track of the ridges 90*a* of the second ring rotator 90, like the relation between the ridges 88*c* and the ridges 90*a*. The third rod rotator 92 also has a stop flange 92*b* on a front side of the ridges 92*a*, the stop flange 92*b* limiting axial movement of the third rod rotator 92 within the rotary shaft 54. The third rod rotator 92 further has a spiral cam groove 92*c* formed around an outer periphery of a front portion forward from the stop flange 92*b*.

The front portion of the third rod rotator 92 is inserted through a hollow of a tubular member 94. The tubular member 94 has protrusions 94*a* formed on its inner periphery such that the protrusions 94*a* are engaged in the cam groove 92*c* of the third rod rotator 92. The tubular member 94 is united with the second lens element 40 through an arm 96. Thus, the tubular member 94 is limited in rotational movement around the third rod rotator 92.

Now the operation of the lens drive mechanism 36 for converting the torsional motion of the drive shaft 56 of the motor 50 to the axial movement of the second lens element 40 will be described.

When the motor 50 is actuated to rotate its drive shaft 56, the motion is transferred from the drive shaft 56 through the first to third gears 76 to 80 of the power transmission mechanism 52 to the first rod rotator 84 of the rotary shaft 54, thereby rotating the first rod rotator 84.

Figure 6B:
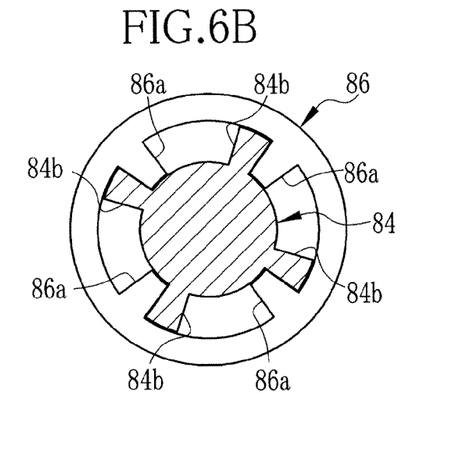

In an initial stage before the motor 50 is actuated, the first rod rotator 84 is set in a neutral position where the ridges 84*b* are placed in between the ridges 86*a* of the first ring rotator 86, as shown in FIG. 6A. When the first rod rotator 84 rotates through an angle of about 20° from the neutral position, the ridges 84*b* come to contact with the ridges 86*a* of the first ring rotator 86, as shown in FIG. 6B. Thereafter, as the first rod rotator 84 further rotates in the same direction, the first ring rotator 86 starts rotating together with the first rod rotator 84.

In the initial stage, the first ring rotator 86 is set in a neutral position where the ridges 86*a* are placed in between the ridges 88*a* of the second rod rotator 88. When the first ring rotator 86 rotates through an angle of about 20° from the neutral position, the ridges 86*a* come to contact with the ridges 88*a*. Thereafter, as the first ring rotator 86 further rotates in the same direction, the second rod rotator 88 starts rotating together with the first ring rotator 86.

Figure 7B:
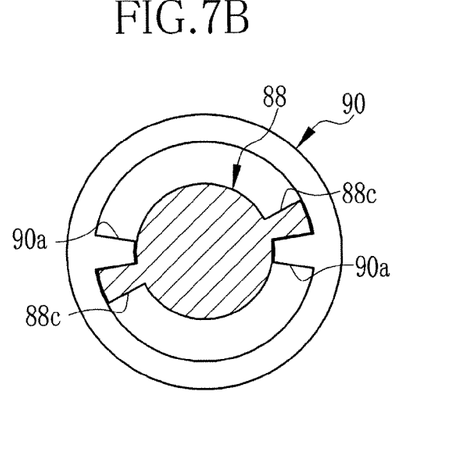

In the initial stage, the second rod rotator 88 is set in a neutral position where the ridges 88*c* are placed in between the ridges 90*a* of the second ring rotator 90, as shown in FIG. 7A. When the second rod rotator 88 rotates through an angle of about 80° from the neutral position, the ridges 88*c* come to contact with the ridges 90a of the second ring rotator 90, as shown in FIG. 7B. Thereafter, as the second rod rotator 88 further rotates in the same direction, the second ring rotator 90 starts rotating together with the second rod rotator 88.

In the initial stage, the second ring rotator 90 is set in a neutral position where the ridges 90a are placed in between the ridges 92a of the third rod rotator 92. When the second ring rotator 90 rotates through an angle of about 80° from the neutral position, the ridges 90a come to contact with the ridges 92a, so that the third rod rotator 92 starts rotating together with the second ring rotator 90 as the second ring rotator 90 further rotates in the same direction. With the rotation of the third rod rotator 92, the protrusions 94a of the tubular member 94 are pushed by the cam groove 92, causing the tubular member 94 to move in the axial direction of the third rod rotator 92. Thus the second lens 40 moves together with the tubular member 94 in the axial direction.

Because the rotary shaft 54 is divided into several segments (rotators) and these segments are coupled to each other through such mechanisms that have a certain play in the rotational direction, the number of segments that are driven to rotate together will increase gradually till the last rotating segment, i.e. the third rod rotator 92 begins to rotate. Thereby, the rotary inertia will gradually increase. This configuration may reduce the load on the motor in comparison with a case where a driven rotary shaft is constructed as an integral member, so that the rotary shaft 54 can stably rotate with a small driving force of the motor 50. Since the rotary shaft 54 provides a certain time lag from the start of motor rotation to the start of lens movement, the movable lens will not overreact on the motion of the motor. Moreover, the rotary shaft constructed as an integral member will increase the weight of the part to be initially driven by the motor to start the lens movement. The increased weight of the initially driven part needs the greater rotary torque for the motor. As a result, the lens will move with a greater stride, making fine-adjustment of the lens position difficult. On the contrast, this problem would not occur in the above-described embodiment of the present invention.

Indeed the load on the motor will increase with the increasing number of shaft segments to be driven to rotate together, but the present embodiment is configured to make the rotary play between the adjacent segments greater as the number of segments rotated together increases; the rotary play between the first rod rotator 84 and the first ring rotator 86 as well as the rotary play between the first ring rotator 86 and the second rod rotator 88 is at most about 40°, while the rotary play between the second rod rotator 88 and the second ring rotator 90 as well as the rotary play between the second ring rotator 90 and the third rod rotator 92 is at most about 160°. According to this configuration, the rotary inertia and hence the speed of the force applied to the next driven segment will increase with the increasing number of rotating segments, reducing the load on the motor in comparison with a case where an equal rotary play is provided between the respective segments.

Now the operation of changing the image magnification by the motor 50 under the control of the processor unit 11 will be described.

Figure 8:
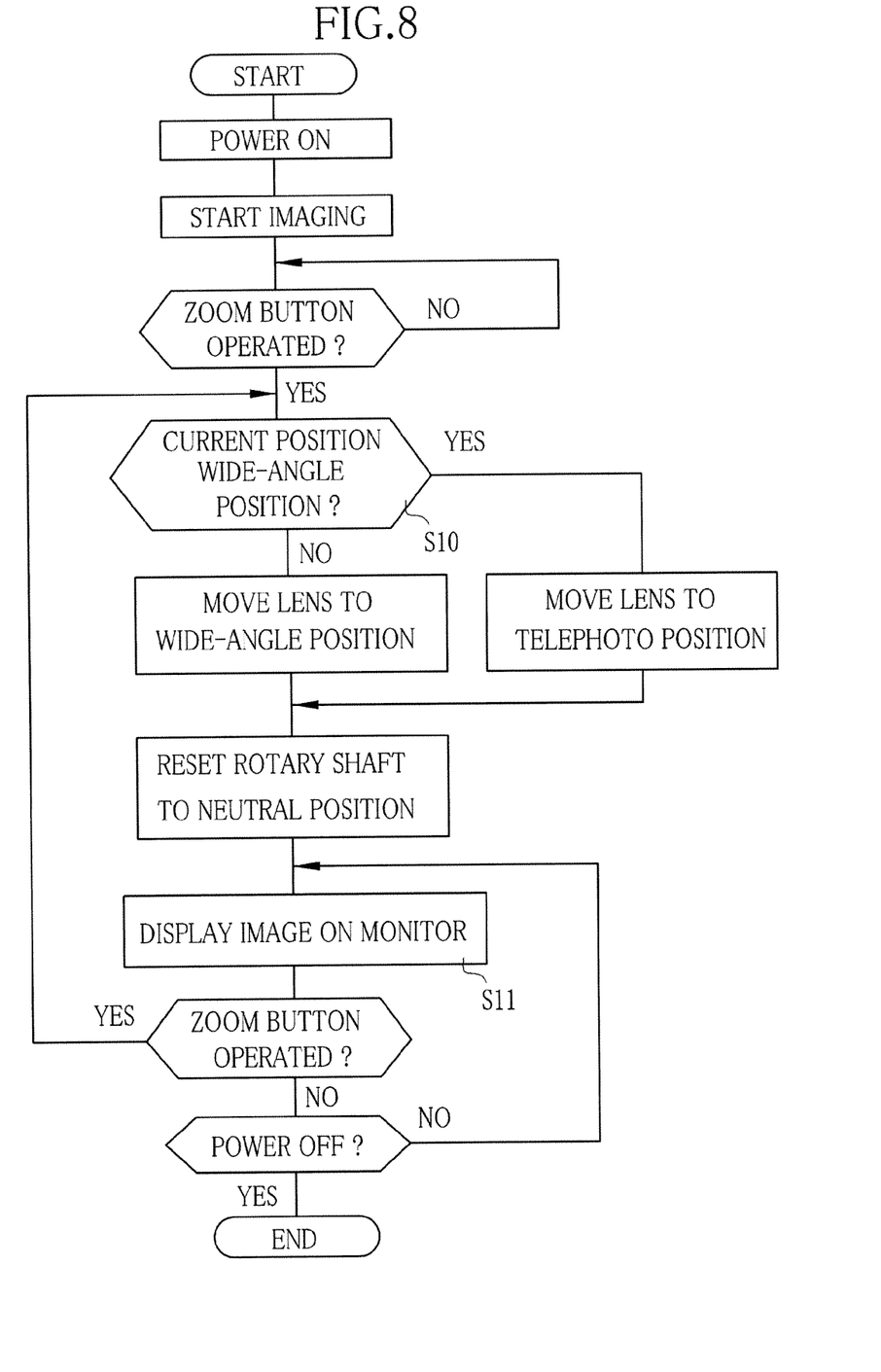
FIG. 8 is a flowchart illustrating a sequence of operations of the electronic endoscope.

As shown in FIG. 8, when the processor unit 11 is powered on, the processor unit 11 starts power-supply to the camera module 30 and controls the circuit board 34 to start imaging the inside of the test body cavity. Then the acquired images are displayed on the monitor 12. Next, whether the zoom button 21 is pushed on or not is judged. If the zoom button 21 is pushed on, the step returns to S10. If the zoom button 21 is not pushed on, whether the processor unit 11 is powered off or not is judged. If the processor unit 11 is powered off, the operation ends. If the processor unit 11 is not powered off, the step returns to S11.

Each time the zoom button 21 is pushed on, the processor unit 11 controls the motor 50 to switch over the second lens element 40 between a reducing position (wide-angle position) on the side of the first lens element 38, and an enlarging position (telephoto position) on the side of the third lens element 42. Each time the second lens element 40 is switched over to the other position, the processor unit 11 controls the motor 50 to reset the respective segments of the rotary shaft 54 to the neutral positions.

Specifically, when the second lens element 40 stops at one switching position (the wide-angle position or the telephoto position), the processor unit 11 drives the motor 50 to run in the opposite direction (referred to as the reverse direction here) to the preceding running direction (referred to as the forward direction here), to rotate the second ring rotator 90 through an angle of about 80° to reset it to the neutral position. Thereafter, the motor 50 is driven in the forward direction to rotate the second rod rotator 88 through an angle of about 80° to reset it to the neutral position. Then the motor 50 is driven again in the reverse direction to rotate the first ring rotator 86 through an angle of about 20° to reset it to the neutral position. Finally, the motor 50 is driven again in the forward direction to rotate the first rod rotator 84 through an angle of about 20° to reset it to the neutral position.

In the above embodiment, the rotary shaft 54 is disposed on the opposite radial side of the objective lens system 32 to the circuit board 34, wherein the rotary axis of the rotary shaft 54 and the optical axis of the taking lens extend in a common perpendicular plane to the circuit board 34 (see FIG. 3). In another embodiment, as shown for example in FIG. 9, the rotary axis of the rotary shaft 54 may extend in a position leaned to one side from the perpendicular plane to the circuit board 34, the plane including the optical axis of the objective lens system 32.

Figure 10:
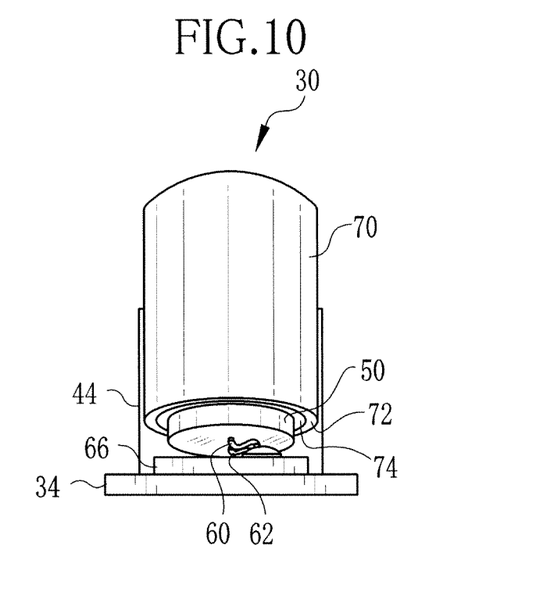
FIG. 10 is a rear view of a camera module of a third embodiment.
Figure 11:
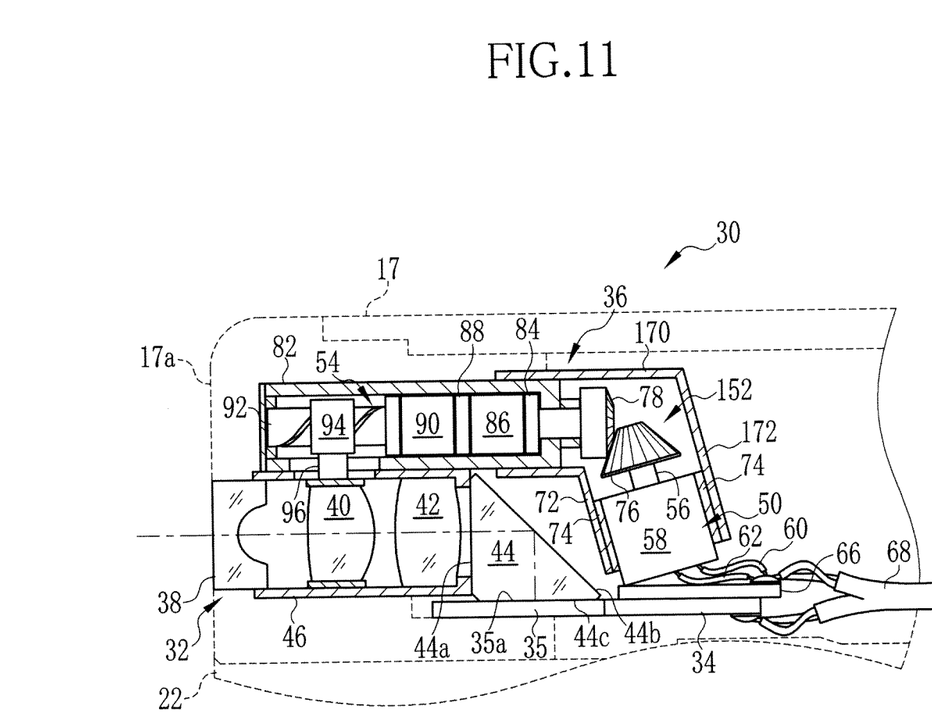
FIG. 11 is a sectional view of the camera module of the third embodiment, taken along an optical axis of a taking lens.

In another embodiment, as shown in FIGS. 10 and 11, a motor 50 may be mounted in a motor case 170 with a drive shaft 56 inclined to an optical axis of a taking lens, when the motor case 170 is disposed behind the prism 44. Also in this embodiment, the optical axis of the taking lens extends in the longitudinal direction of the probing portion 13, and a rotary shaft 54 of a lens drive mechanism 36 is mounted on one radial side of the taking lens, to be rotatable on a rotary axis that is substantially parallel to the optical axis. The motor case 170 is provided with a holder 172 which is formed from a highly exoergic material like aluminum, and a cylindrical body 58 of the motor 50 is adhered to an inner periphery of the holder 72 with a highly heat-conducive adhesive material 74.

The drive shaft 56 is coupled to the rotary shaft 54 through a power transmission mechanism 152 consisting of first and second gears 76 and 78. These gears 76 and 78 are mounted rotatable in the motor case 170. The first gear 76 is affixed to a front end of the drive shaft 56 and rotates together with the drive shaft 56. The second gear 78 is in mesh with the first gear 76 and rotates along with the first gear 76. The motor case 70 shields the mechanism 152 from outside so as to prevent diffusion of dust and dirt to the outside, which may result from the gearing motion. It may be preferable to provide a spring between the second gear 78 and the motor case 170 to press the second gear 78 against the first gear 76.

The second gear 78 is coupled at its front end to the rotary shaft 54, which is mounted rotatable in a cylindrical case 82. The shaft case 82 is placed on the opposite side of the objective lens system 32 to the circuit board 34 such that the rotary axis of the rotary shaft 54 extends substantially parallel to the optical axis of the taking lens 38 to 42 of the objective lens system 32, which extends along the length of the probing portion 13.

Figure 9:
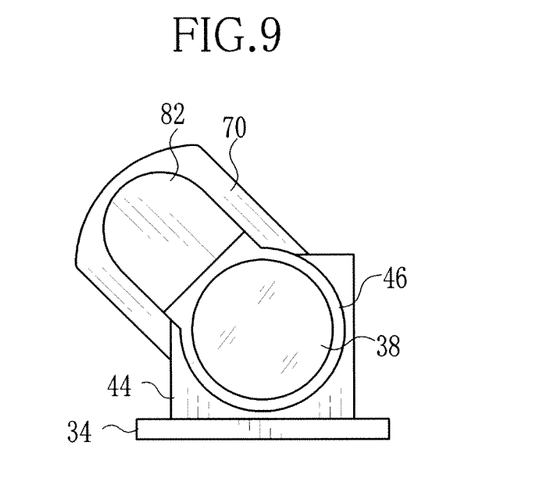
FIG. 9 is a front view of a camera module of a second embodiment.

The rotary shaft 54 may have the same structure as shown in FIG. 5, wherein the rotary shaft 54 consists of a first rod rotator 84, a first ring rotator 86, a second rod rotator 88, a second ring rotator 90, and a third rod rotator 92, which are aligned in this order from the third gear 80 toward the end face 17a, so as to be rotatable on the common rotary axis. The first rod rotator 84 is affixed at its rear end to the second gear 78 so that it rotates together with the second gear 78. Otherwise, the rotary shaft 54 may operate in the same way as described above with reference to FIGS. 6 to 8. Also the lens drive mechanism 36 structured as shown in FIGS. 10 and 11 may be positioned such that the rotary shaft 54 extends along a position leaned to one side from the opposite position to the circuit board 34 across the optical axis of the objective lens system 32, like as shown in FIG. 9.

Although the present invention has been described with reference to the illustrated embodiments, the present invention should not be limited to these embodiments but may be modified appropriately insofar as the motor is disposed behind the prism thereby to increase the space efficiency and make the camera module compact and small. For example, the inclination angle of the drive shaft of the motor to the rotary shaft may be determined appropriately. Moreover, the rotary shaft may be constructed as an integral member, although the rotary shaft is constituted of the five rotators in the above embodiment. Furthermore, the number of rotators constituting the rotary shaft is not limited to five, but less than or more than five rotators may constitute a rotary shaft.

Although the motor used in the above embodiment is described as a DC motor, the motor may be a stepping motor that rotates its drive shaft by an angle according to the number of applied drive pulses. With such a stepping motor, fine control of rotary motion of the rotators (the members constituting the rotary shaft) and hence fine control of lens movement can be more easily performed.

In the above embodiment, the rotators constituting the rotary shaft are reset to the respective neutral positions after the movable lens is stopped. However, this resetting operation is not always necessary. The motor may stop immediately after stopping the movable lens at a designated position. Alternatively, the lens drive mechanism may be configured such that some of the segments of the rotary shaft are reset to their neutral positions after each zooming operation.

It is also possible to control the motor 50 to run in the reverse direction by a half amount of an idling rotation of the motor, which is to be made in order to invert the moving direction of the movable lens. Specifically, in a case where the first segment of the rotary shaft must be rotated through an angle of about 400° in the reverse direction in order to move the movable lens in the opposite direction to the preceding moving direction, like in the embodiment of FIG. 5, wherein the first rod rotator 84 must be rotated about 40° in the reverse direction to cause the first ring rotator 86 to start rotating in the reverse direction, and then the first ring rotator 86 must be rotated about 40° in the reverse direction to cause the second rod rotator 88 to start rotating in the reverse direction, and thereafter the second rod rotator 88 must be rotated about 160° in the reverse direction to cause the second ring rotator 90 to start rotating in the reverse direction, and finally the second ring rotator 90 must be rotated about 160° in the reverse direction to cause the third rod rotator 92 to start rotating in the reverse direction, the motor 50 may be driven in the reverse direction to rotate the first rod rotator 84 about 200° in the reverse direction after the movable lens is stopped at a designated position.

In the above embodiment, the rotary play between the adjacent segments of the rotary shaft increases in two steps from the first rotating segment to the last. It is alternatively possible to provide rotary play of an equal amount between the respective segments. It is also possible to increase the amount of rotary play in more than two steps. For example, the rotary play between a first rod rotator and a first ring rotator may be set at most 20°, the rotary play between the first ring rotator and a second rod rotator may be set at most 40°, the rotary play between the second rod rotator and a second ring rotator may be set at most 80°, and the rotary play between a second ring rotator and a third ring rotator may be set at most 160°.

Although the rotary motion of the rotary shaft 54 is converted to the axial movement of the movable lens 40 through the engagement between the spiral cam groove 92c around the third rod rotator 92 and the cam protrusions 94a on the inner periphery of the tubular member 94 in the above embodiment, the rotary motion of the rotary shaft 54 may be converted to the axial movement of the movable lens 40 through another mechanism. For example, a spiral cam groove may be provided around an inner periphery of a tubular member that is not rotatable and fixedly coupled to the movable lens, while at least a cam protrusion may be provided on an outer periphery of a rotary shaft or a rod segment thereof, which extends through the tubular member. It is also possible to provide a female thread and a male thread around the inner periphery of the tubular member and the outer periphery of the rod segment of the rotatory shaft, respectively. It should be appreciated that a female thread may be provided around the inner periphery of the tubular member and a male thread may be provided around the outer periphery of the rod segment of the rotatory shaft.

Although the movable lens is moved either to the wide-angle position or to the telephoto position changing the image magnification in two steps in the above embodiment, the movable lens may be moved in three or more steps. It is also possible to construct the taking lens as a non-step zoom lens.

Although the embodiments of the present invention have been described with respect to the camera module where the motor 50 drives the movable zoom lens 40 for changing the image magnification, the present invention is also applicable to a camera module where a motor for driving a movable focusing lens is disposed behind a prism of an objective lens system. It may also be possible to dispose two motors for driving a movable zoom lens and a movable focusing lens, respectively.

The imaging device used in the camera module is not limited to a CCD image sensor, but may be a CMOS image sensor or the like. It is not necessary to provide a cylindrical case for a rotary shaft separately from a lens barrel for a taking lens, but they may be formed as an integral member. The present invention is applicable not only to medical endoscopes but also to industrial endoscopes.

It should be understood that the embodiments of the present invention have been disclosed for illustrative purposes only. Those skilled in the art will appreciate that various modifications, additions and substitutions are possible without departing from the scope and spirit of the invention as disclosed in the accompanying claims.

What is claimed is:

1. A camera module for an endoscope, comprising:
   a taking lens having a lens element movable along an optical axis thereof;

a prism positioned behind the taking lens, the prism reflecting incident light at an approximately right angle to the optical axis;

a circuit board having an imaging device mounted thereon, the imaging device having an imaging surface on which an optical image is formed through the taking lens and the prism, the imaging device converting the optical image to an electric signal; and a lens drive mechanism for moving the movable lens element, comprising:

a motor positioned in a distal end of the endoscope and behind the prism, the motor being driven to rotate a drive shaft upon an externally supplied electric power;

a rotary shaft positioned on one radial side of the taking lens, the rotary shaft being rotatable on an axis extending along the optical axis, the rotary shaft being coupled to the movable lens element such that bidirectional rotary motions of the rotary shaft cause the movable lens element to move back and forth along the optical axis; and a power transmission mechanism for transmitting the rotary motions of the drive shaft to the rotary shaft, wherein the rotary shaft consists of a number of rotators aligned to be rotatable on a common axis that is parallel to the optical axis, wherein adjacent two of the rotators are coupled to each other with a predetermined rotary play, to transmit the rotary motion of the drive shaft sequentially from a rear side one of the rotators, which is coupled to the power transmission mechanism, toward a front side one of the rotators, which is coupled to the movable lens.

2. The camera module as recited in claim 1, wherein the rotary shaft consists of at least three rotators, wherein the rotary play between the adjacent two rotators is set at a larger angle in the front side than in the rear side.

3. The camera module as recited in claim 1, wherein the rotators include at least a rod rotator and at least a ring rotator, which are aligned alternately on the common axis, wherein the rod rotator has outward protrusions provided at regular angular intervals around an outer periphery thereof, and the ring rotator has inward protrusions provided at regular angular intervals around an inner periphery thereof, and has a greater internal diameter exclusive of the inward protrusions than an external diameter of the rod rotator inclusive of the outward protrusions, the ring rotator being rotatably fitted on the rod rotator and caused to rotate together with the rod rotator as the outward protrusions push the inward protrusions when the rod rotator rotates inside the ring rotator.

4. The camera module as recited in claim 1, wherein, after the movable lens element is moved into a designated position before the motor being stopped, the motor is driven to rotate the drive shaft in a reverse direction opposite to a preceding rotational direction or alternately in the reverse and opposite directions to the extent that it does not cause the movement of the movable lens element, thereby to reset the rotators to neutral positions, from these neutral positions the drive shaft may be rotated by an approximately equal amount in either direction till all the rotators begin to rotate together.

5. The camera module as recited in claim 1, wherein the taking lens, the prism, the circuit board and the lens drive mechanism are formed in the distal end of the endoscope.

6. The camera module as recited in claim 1, wherein the endoscope comprises a probing portion and the camera module is formed in a distal end of the probing portion.

7. A lens drive mechanism for moving a movable lens element of a taking lens in a camera module of an endoscope, the lens drive mechanism comprising:

a motor positioned behind a prism of the camera module, the motor being driven to rotate a drive shaft upon an externally supplied electric power;

a rotary shaft positioned on a radial side of the taking lens, the rotary shaft being rotatable on a parallel axis which is parallel to an optical axis of the taking lens, the rotary shaft being coupled to the movable lens element such that bidirectional rotary motions of the rotary shaft cause the movable lens element to move back and forth along the optical axis; and a power transmission mechanism for transmitting a rotary motion of the drive shaft to the rotary shaft, wherein the rotary shaft comprises a plurality of rotators aligned to be rotatable on the parallel axis, the plurality of rotators comprising:

a first rotator coupled to the power transmission mechanism; and a second rotator coupled to the movable lens, and coupled to the first rotator with a predetermined rotary play, the rotary motion of the drive shaft being transmitted sequentially from a rear side of the first rotator toward a front side of the second rotator.

\* \* \* \* \*